(12) United States Patent
Zhang et al.

(10) Patent No.: US 10,595,865 B2
(45) Date of Patent: Mar. 24, 2020

(54) ELECTRIC SURGICAL STAPLER

(71) Applicant: SUZHOU INTOCARE MEDICAL TECHNOLOGY CO., LTD, Suzhou (CN)

(72) Inventors: Hui Zhang, Suzhou (CN); Yunfeng Du, Suzhou (CN); Dianchen Liu, Suzhou (CN); Aiyu Huang, Suzhou (CN)

(73) Assignee: Suzhou Intocare Medical Technology Co., Ltd., Suzhou (CN)

( * ) Notice: Subject to any disclaimer, the term of this patent is extended or adjusted under 35 U.S.C. 154(b) by 326 days.

(21) Appl. No.: 15/567,164

(22) PCT Filed: Jul. 29, 2016

(86) PCT No.: PCT/CN2016/092395
§ 371 (c)(1),
(2) Date: Oct. 17, 2017

(87) PCT Pub. No.: WO2017/133205
PCT Pub. Date: Aug. 10, 2017

(65) Prior Publication Data
US 2018/0092640 A1 Apr. 5, 2018

(30) Foreign Application Priority Data
Feb. 3, 2016 (CN) .......................... 2016 1 0076148

(51) Int. Cl.
*A61B 17/072* (2006.01)
*A61B 17/11* (2006.01)
(Continued)

(52) U.S. Cl.
CPC ...... *A61B 17/07207* (2013.01); *A61B 17/072* (2013.01); *A61B 17/1114* (2013.01);
(Continued)

(58) Field of Classification Search
CPC .. A61B 2017/07214; A61B 2017/0725; A61B 2017/07257
(Continued)

(56) References Cited

U.S. PATENT DOCUMENTS

| 6,981,941 B2 * | 1/2006 | Whitman | ........... A61B 10/0233 227/175.1 |
| 8,286,846 B2 * | 10/2012 | Smith | ................. A61B 17/1114 227/175.1 |

(Continued)

FOREIGN PATENT DOCUMENTS

| CN | 102151157 A | 8/2011 |
| CN | 102247182 A | 11/2011 |

(Continued)

OTHER PUBLICATIONS

International Search Report for International Application No. PCT/CN2016/092395 dated Nov. 3, 2016, 5 pages.
(Continued)

*Primary Examiner* — Gloria R Weeks
(74) *Attorney, Agent, or Firm* — Seyfarth Shaw LLP

(57) ABSTRACT

The present disclosure relates to an electric surgical stapler, including a handle the handle having a handle body, a driving motor and a control unit for controlling the driving motor to operate; a working head, including an anvil, a cartridge, a closing mechanism, a firing mechanism, a housing for accommodating the closing mechanism and the firing mechanism, a closing limit switch, and a closing height adjustment shift switch configured to transmit information of a closing height control shift to the control unit, wherein during closing, the control unit is configured to control the closing mechanism to move until the closing limit switch is triggered so that a closing distance between the anvil and the cartridge is at a preset closing height, and the control unit is further configured to control the closing mechanism to move (Continued)

after receiving information transmitted from the closing limit switch, so that the closing distance between the anvil and the cartridge is adjusted to be consistent with a preset closing distance corresponding to a current shift of the closing height adjustment shift switch. Since a certain distance is closed in advance, clearances in the transmission mechanism have been eliminated, and the adjustment of the closing height can be accurately implemented to achieve desired closing height.

10 Claims, 3 Drawing Sheets

(51) Int. Cl.
*A61B 17/115* (2006.01)
*A61B 17/00* (2006.01)
(52) U.S. Cl.
CPC . *A61B 17/1155* (2013.01); *A61B 2017/00022* (2013.01); *A61B 2017/00039* (2013.01); *A61B 2017/00398* (2013.01); *A61B 2017/00734* (2013.01); *A61B 2017/0725* (2013.01); *A61B 2017/07257* (2013.01); *A61B 2017/07271* (2013.01); *A61B 2017/07285* (2013.01)
(58) Field of Classification Search
USPC ..................................... 227/175.3
See application file for complete search history.

(56) References Cited

U.S. PATENT DOCUMENTS

| | | | | |
|---|---|---|---|---|
| 9,579,100 | B2* | 2/2017 | Castro | .................. A61B 17/068 |
| 10,278,698 | B2 | 5/2019 | Racenet | |
| 2007/0187453 | A1* | 8/2007 | Smith | .............. A61B 17/07207 227/175.1 |
| 2010/0089972 | A1* | 4/2010 | Marczyk | .......... A61B 17/07207 227/178.1 |
| 2010/0096431 | A1* | 4/2010 | Smith | .................... A61B 17/00 227/175.2 |
| 2012/0116427 | A1 | 5/2012 | Raza | |
| 2014/0305992 | A1 | 10/2014 | Kimsey et al. | |
| 2015/0048140 | A1 | 2/2015 | Penna | |

FOREIGN PATENT DOCUMENTS

| | | |
|---|---|---|
| CN | 202184762 U | 4/2012 |
| CN | 103142240 A | 6/2013 |
| CN | 202982103 U | 6/2013 |
| CN | 103181795 A | 7/2013 |
| CN | 103784175 A | 5/2014 |
| CN | 104116538 A | 10/2014 |
| CN | 204364051 U | 6/2015 |
| CN | 105496488 A | 4/2016 |
| EP | 2491872 A1 | 8/2012 |

OTHER PUBLICATIONS

Written Opinion for International Application No. PCT/CN2016/092395 dated Oct. 21, 2016, 5 pages.
Chinese Office Action for Application No. 201610076148.2 dated Jun. 2, 2017, 5 pages.
Chinese Search Report for Application No. 201610076148.2 dated Feb. 3, 2016, 1 page.
European Search Report for Application No. 16889020.0 dated Sep. 5, 2019, 8 pages.

* cited by examiner

ELECTRIC SURGICAL STAPLER

CROSS REFERENCE TO RELATED APPLICATIONS

This is a National Stage application of PCT/CN2016/092395, filed Jul. 29, 2016, and claims priority to Chinese Patent Application Serial No. CN 201610076148.2, filed Feb. 3, 2016, the disclosures of which are incorporated herein by reference.

TECHNICAL FIELD

The present disclosure relates to the technical field of medical equipment, and more particularly, to an electric surgical stapler.

BACKGROUND

The surgical stapler is a common medical device when performing a surgical procedure on tissues of the digestive tract. During the surgical treatment, the surgical stapler is often use in tissue cutting and stitching. The surgical stapler may perform closing, stapling or cutting operations on the physiological tissue manually or electrically.

The manual operation implements the closing action between the anvil and the cartridge, and the firing action on the tissue to be stapled in a purely mechanical way. The process of the firing needs huge firing force to complete the cutting and closing of the anastomotic stoma, with high requirement for the user. It is easy to cause the mechanical firing to fail once the skills and the strength of force and not mastered properly. The closing effect of the tissue will be affected by inadequate firing force, to cause inadequate cutting and closing, resulting in failure of surgery, and extremely high risk. There is no risk of inadequate firing force for an electric surgical stapler as long as it has adequate power.

A surgeon needs to choose an appropriate tissue squeezing degree (from 1.5 mm to 2.5 mm within a green zone range) according to characteristics of the tissue for different patients at the time of surgery, but closing height shown in the indication window for green zone range of the existing pure mechanical stapler is an approximate display amplified by a mechanical structure. Since the manufacturing error of the mechanical parts, there exists a significant error between the height of the indication window and the actual closing height of the tissue. Therefore, the error caused by only observing the closing height window to determine the squeezing thickness of the tissue may lead to large discreteness of postoperative effects of different patients, which not only affects the efficiency of the surgery, but also causes inconsistent staple formations, two-step staple formation, and other phenomena. In this case, there may appear tissue leakage, tissue necrosis or other postoperative symptoms. For the linear closer and cutter, the general method is to use cartridges of different heights to form staples of different heights in a unified device's closing height. This method costs too many numbers and types of the cartridges, and it does not only affects the efficiency of the surgery, but also may causes the usage of a wrong type of cartridge during an operation under certain circumstance due to the complexity of device management.

SUMMARY

Based on the above, an objective of the present disclosure is to provide an electric surgical stapler, which can effectively ensure the desired tissue closing height is consistent with the actual tissue squeezing thickness.

According to an aspect of the present disclosure, an electric surgical stapler is provided, including: a handle, which includes handle body itself, a driving motor and a control unit for controlling the driving motor to operate; a working head, which includes an anvil, a cartridge, a closing mechanism, a firing mechanism, a housing for accommodating the closing mechanism and the firing mechanism, a closing limit switch configured to transmit information of a closing stroke of the closing mechanism to the control unit, and a closing height adjustment shift switch configured to transmit information of a closing height control shift to the control unit, wherein during closing, the control unit is configured to control the closing mechanism to move until the closing limit switch is triggered so that a closing distance between the anvil and the cartridge is at a preset closing height, and the control unit is further configured to control the closing mechanism to move after receiving information transmitted from the closing limit switch, so that the closing distance between the anvil and the cartridge is adjusted to be consistent with a preset closing distance corresponding to a current shift of the closing height adjustment shift switch.

For the above electric surgical stapler, when the closing limit switch detects that the closing distance between the anvil and the cartridge is at the preset closing height, the control unit controls the closing mechanism to continue to move to adjust the closing distance according to the information of the shift where the closing height adjustment shift switch is, and only when the closing distance is consistent with the preset closing distance corresponding to the current shift of the closing height adjustment shift switch, the control unit transmits a firing instruction. In this way, there is no excessive or inadequacy squeezing, so it can ensure the tissue is squeezed adequately regardless of the thickness, and to ensure the stable effect of the staple formation. Since the device is closed to a maximum height (i.e., a position where the closing optoelectronic switch is triggered) in advance, clearances in the transmission mechanism have been eliminated, and on this basis, the subsequent adjustment of the closing height can be accurately implemented to achieve desired closing height, replacing the old manual adjustment of the closing height. For the case where the height is required to be adjusted, the surgeon only needs to shift the closing height adjustment shift switch to a corresponding shift, to ensure stable effect of the staple formation.

In addition, the electric surgical stapler also reduces the complexity of preparing devices for surgery. The user can use a single electric surgical stapler to form staples of different heights by setting different closing heights, without using cartridges of different closing heights, to simply and effectively ensure the postoperative effect.

In one embodiment, the working head further includes a firing limit switch configured to transmit information of a firing stroke to the control unit, and when the firing limit switch is triggered, the control unit stops the operation of the driving motor.

In one embodiment, the working head further includes a firing safety switch, the firing safety switch has a first operating position and a second operating position, the firing safety switch allows the driving motor to drive the closing mechanism to operate when the firing safety switch is at the first operating position, and the firing safety switch allows the driving motor to drive the firing mechanism to operate when the firing safety switch is at the second operating position.

In one embodiment, the closing mechanism includes a first linear motion component configured to drive the anvil to move or drive the cartridge to move, and the firing mechanism includes a second linear motion component configured to push a staple ejecting plate in the cartridge to move.

In one embodiment, the closing mechanism includes a closing main shaft driven by an output shaft of the driving motor to rotate, the first linear motion component is configured to be driven by the closing main shaft and drive the anvil to move, the firing mechanism includes a firing main shaft driven by the output shaft of the driving motor to rotate, and the second linear motion component is configured to be driven by the firing main shaft and act on the staple ejecting plate in the cartridge.

In one embodiment, the electric surgical stapler further includes a firing safety switch having a first operating position and a second operating position, the firing safety switch allows the output shaft to transmit torque to the closing main shaft when the firing safety switch is at the first operating position, and the firing safety switch allows the output shaft to transmit torque to the firing main shaft when the firing safety switch is at the second operating position.

In one embodiment, a closing switch and an opening switch connected to the control unit are arranged outside the handle body, the control unit is further configured to transmit an instruction of controlling the driving motor to drive the closing main shaft to move when detecting that the closing switch is triggered and the firing safety switch is at the first operating position, and the control unit is further configured to transmit an instruction of controlling the driving motor to drive the firing main shaft to move when detecting that the closing switch is triggered and the firing safety switch is at the second operating position.

In one embodiment, the electric surgical stapler further includes a firing limit switch configured to detect a position of the second linear movement component and transmit position information of the second linear movement component to the control unit, and the control unit is further configured to stop the operation of the driving motor when the second linear movement component comes within a preset position range and triggers the firing limit switch.

In one embodiment, the closing limit switch is an optoelectronic switch, a micro switch or a proximity switch.

In one embodiment, a manual adjustment knob is arranged on an outer wall of the handle body, and the manual adjustment knob is configured to drive the output shaft to rotate when the manual adjustment knob rotates.

In one embodiment, the housing is removably connected to the handle body, the working head and the driving device are assembled together when the housing is connected to the handle body, and the working head is separated from the driving device when the housing is removed from the handle body.

In one embodiment, a data interface connected to the closing height adjustment shift switch, the closing limit switch, the firing limit switch and the safety switch is arranged inside the handle body, and the data interface is connected to the control unit.

In one embodiment, a release button is arranged outside the handle body, and the release button has a locking position for locking the housing and a release position for unlocking the housing.

In one embodiment, a window for observing the position of the closing main shaft is arranged on the housing.

In one embodiment, the electric surgical stapler further includes a replaceable battery pack configured to be connected to the handle body and supply power to the driving motor.

In one embodiment, a battery level indicator light connected to the control unit is arranged on the handle body.

In one embodiment, the closing height adjustment shift switch is connected to a different circuit when switching shifts, to transmit different electrical signals to the control unit.

In one embodiment, the closing height adjustment shift switch is provided with a plurality of shifts, each shift corresponds to a different preset closing distance, each preset closing distance is different from the closing distance between the anvil and the cartridge when the closing limit switch is triggered, or one of the plurality of present closing distances is the same as the closing distance between the anvil and the cartridge when the closing limit switch is triggered.

DETAILED DESCRIPTION

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

The preferred embodiments of the electric surgical stapler will be described taken in conjunction with the accompanying drawings.

Figure 1:
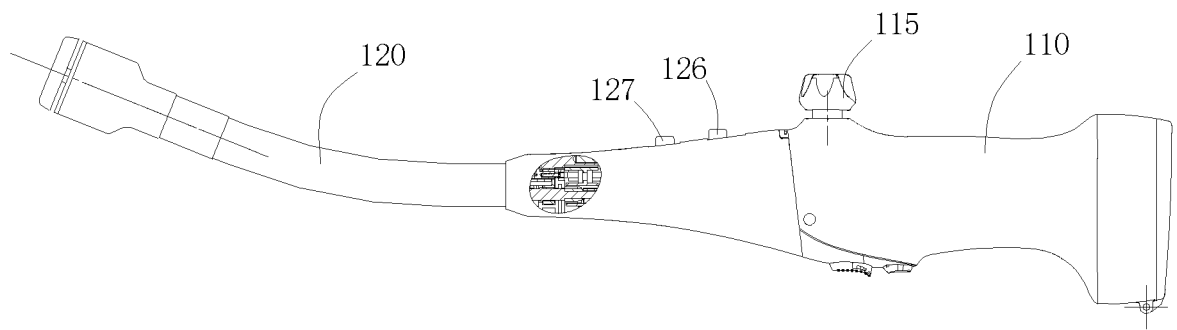
FIG. 1 is a schematic diagram illustrating an electric surgical stapler according to Example One of the present disclosure.

With reference to FIG. 1, an electric surgical stapler is provided, including a handle 110 and a replaceable working head 120.

Figure 2:
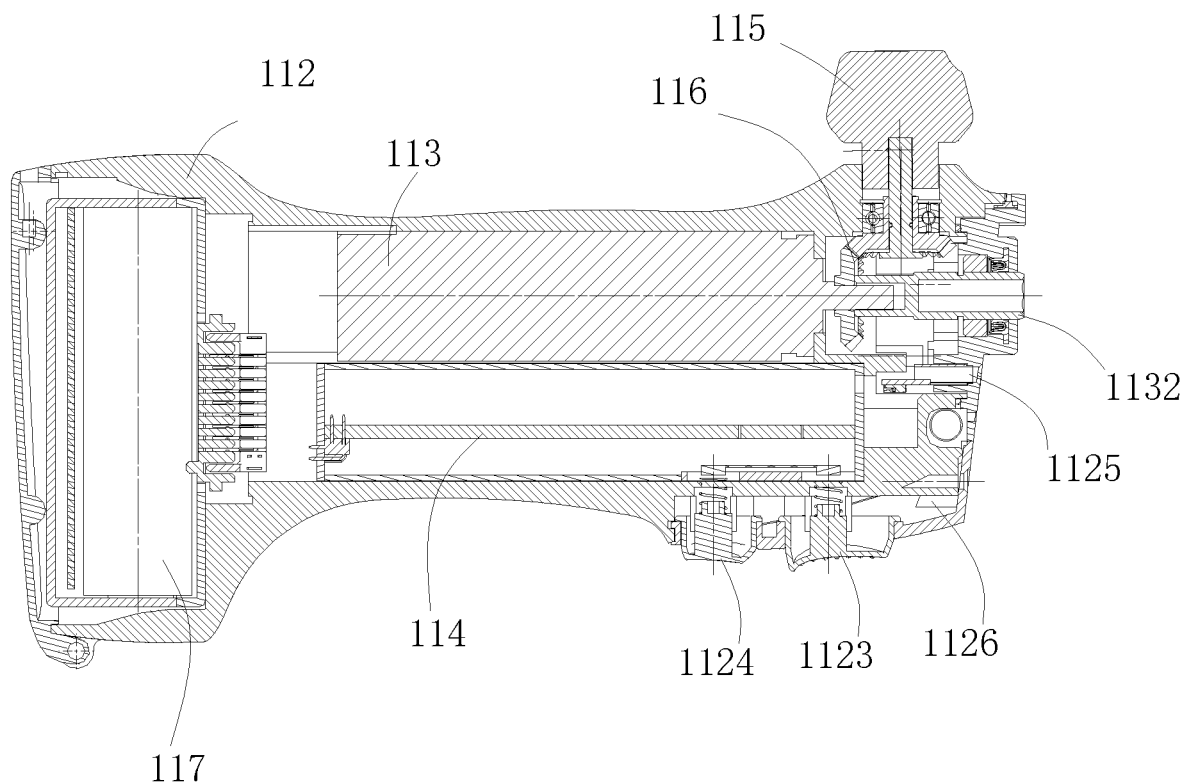
FIG. 2 is a schematic diagram illustrating a handle of the electric surgical stapler according to Example One of the present disclosure.

With reference to FIG. 2, the handle 110 is a driving device for driving the working head 120 to operate, including a hollow handle body 112, a driving motor 113 with an output shaft 1132, and a control unit 114, and the driving motor 113 and the control unit 114 are arranged inside the handle body 112.

The outer wall of the handle body 112 is provided with an adjustment knob 115. The adjustment knob 115 is connected to the output shaft 1132 through a bevel gear system 116. When the driving motor 113 stops, the user may turn the adjustment knob 115, and the bevel gear system 116 may drive the output shaft 1132 to rotate, to achieve manual adjustment. In this way, when there is a failure in the electric system, the adjustment knob 115 may be pulled out upwards to enable the manual mode, in which the adjustment knob 115 may be used to open the jaw of the working head 120 or finish firing.

In this example, the working head 120 is a circular stapling head, including an anvil 121, cartridge 122, a closing mechanism, a firing mechanism, a firing safety switch 126, a closing height adjustment shift switch 127 and a housing 125 housing the closing mechanism and the firing mechanism.

The closing mechanism includes a closing main shaft 1232, a closing height adjustment shift switch 127 and a closing transmission mechanism. The closing main shaft 1232 is driven by a driving motor 113 to rotate. The closing transmission mechanism is connected to the anvil 121. When the closing main shaft 1232 rotates, a first linear motion component in the closing transmission mechanism drives the anvil 121 to move in a straight line. The first linear motion component includes a first sliding block 1234 and a first push rod 1235 driven by the first sliding block 1234. The first sliding block 1234 is connected to the closing main shaft 1232 in a helical transmission form, but the rotation of the first sliding block 1234 is limited. When the closing main shaft 1232 rotates, the first sliding block 1234 is able to move in a straight line, and drive the movement of the anvil 121 through the first push rod 1235.

The firing mechanism includes a firing main shaft 1242 and a firing transmission mechanism. The firing main shaft 1242 is driven by the driving motor 113 to rotate. The firing transmission mechanism is connected to a staple ejecting plate. When the firing main shaft 1242 rotates, a second linear motion component in the firing transmission mechanism causes the staple ejecting plate to perform firing actions. In this example, the second linear motion component is similar to the first linear motion component in the closing transmission mechanism. The second linear motion component includes a second sliding block 1244 and a second push rod 1245 driven by the second sliding block 1244. When the firing main shaft 1242 rotates, the second sliding block 1244 is able to move in a straight line, and drive the movement of the staplestaple ejecting components in the cartridge 122 through the second push rod 1435.

The working head 120 further includes a firing safety switch 126 mounted on the housing 125. The firing safety switch 126 has a first operating position and a second operating position. The firing safety switch 126 allows the output shaft 1132 to transmit torque to the closing main shaft 1232 when the firing safety switch 126 is at the first operating position, and the first operating position is defined as a closing position. The firing safety switch 126 allows the output shaft 1132 to transmit torque to the firing main shaft 1242 when the firing safety switch 126 is at the second operating position, and the second operating position is defined as a firing position.

The firing safety switch 126 fits a switching transmission mechanism in the housing 125. The switching transmission mechanism includes an input shaft 1271, a switching shaft 1272, a switching driving lever 1273, a first switching ring 1274, a first guide block 1275, a second switching ring 1276 and a second guide block 1277 matching and connected to the output shaft 1132.

The input shaft 1271 transmits power to the switching shaft 1272 through a gear mechanism. The first guide block 1275 is fastened to the input shaft 1271, the first switching ring 1274 is able to drive the closing main shaft 1232 to rotate, and be driven by the switching driving lever 1273 to be engaged with or disengaged from the first guide block 1275. The second guide block 1277 is fastened to the firing main shaft 1242, the second switching ring 1276 is able to drive the firing main shaft 1242 to rotate, and be driven by the switching driving lever 1273 to be engaged with or disengaged from the second guide block 1277.

The firing safety switch 126 may be operated to drive the switching driving lever 1273, so that the first switching ring 1274 is engaged with the first guide block 1275 while the second switching ring 1276 is disengaged from the second guide block 1277, or the first switching ring 1274 is disengaged from the first guide block 1275 while the second switching ring 1276 is engaged with the second guide block 1277. In this way, the switching of the power transmission can be achieved by operating the firing safety switch 126.

The switching transmission mechanism may be implemented in other forms. For example, an intermediate shaft and a switching member matching and connected to the output shaft 1132 may be provided. The switching member may make an axially upward movement on the intermediate shaft, the switching member may connect the intermediate shaft to the closing main shaft 1232 at the first operating position, and the switching member may connect the intermediate shaft to the firing main shaft 1242 at the second operating position.

The handle 110 is only internally provided one driving motor 113 and one output shaft, and can switch power transmission by the firing safety switch 126. There may also be two driving motors 113, that is one driving motor is adapted to drive the closing main shaft 1232 alone, and the other driving motor is adapted to drive the firing main shaft alone.

Further, the firing safety switch 126 is mounted on the housing 125. The firing safety switch 126 may also be arranged on the handle body 112, that is, the switching mechanism for power transmission may be arranged within the handle 110.

Figure 3:
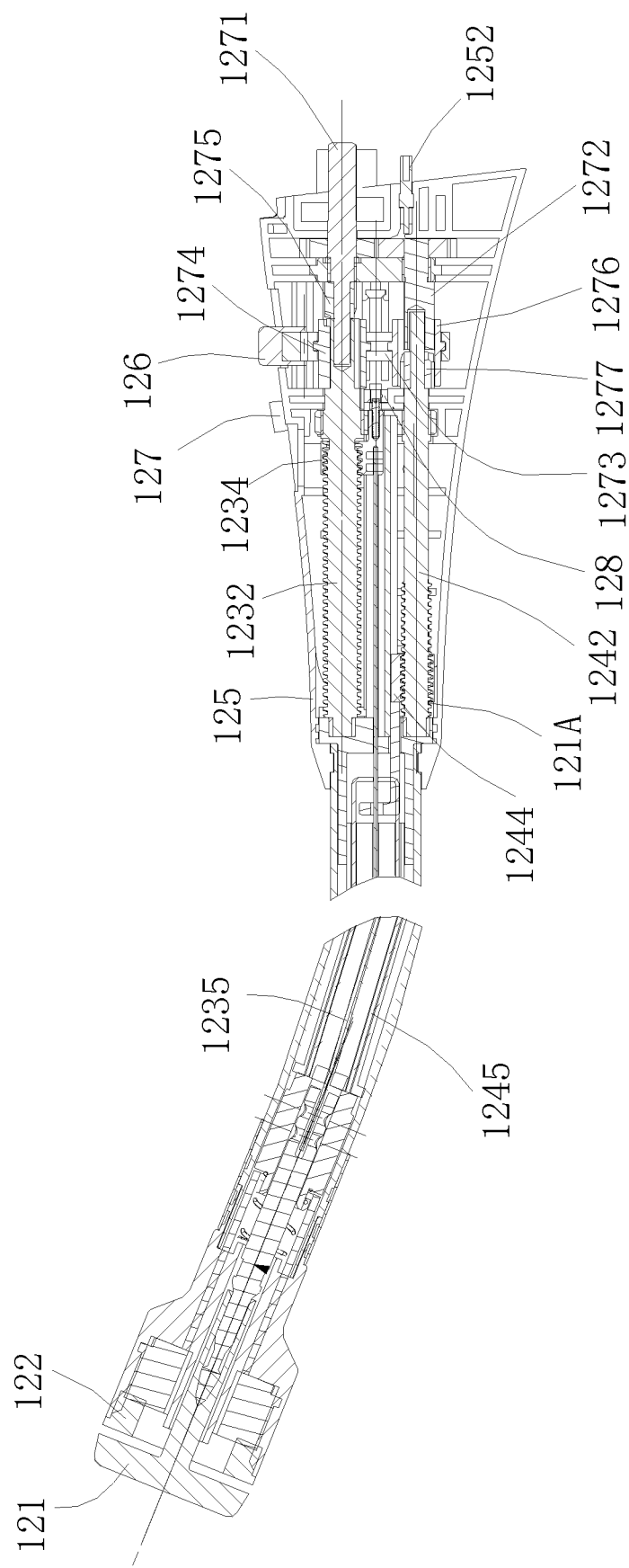
FIG. 3 is a schematic diagram illustrating a circular stapling head in the electric surgical stapler according to Example One of the present disclosure.

With reference to FIG. 3, the working head 120 also includes a closing height adjustment shift switch 127 and a closing limit switch 128.

The closing height adjustment shift switch 127 may be set in a HB (with a maximum closing height of 2.5 mm), MB (with a medium closing height of 2 mm) or LB (with a minimum closing height of 1.5 mm) state. The closing height adjustment shift switch 127 is initially set in the HB state, in which an adjusting screw on the closing main shaft 1232 contacts with the position of the closing limit switch 128 (with a closing height of 2.5 mm). When the closing height adjustment shift switch 127 is shifted to the MB or LB state, the control chip may continue to instruct the motor to make a corresponding number of turns when the distance of the jaw is closed to 2.5 mm, to achieve further closure of the jaw. Since the clearances in the transmission mechanism have been eliminated when distance of the jaw is closed to the HB state (2.5 mm), the jaw can be accurately closed to a preset value by controlling the number of turns made by the motor.

When the closing height adjustment shift switch 127 is switched among the shifts, different circuits may be connected to the control unit 114, to transmit different electrical signals to the control unit 114, so the control unit 114 can identify the current shift of the closing height adjustment shift switch 127.

The closing limit switch 128 is configured to detect the closing stroke of the closing mechanism, and transmit information of the closing stroke to the control unit 114. The closing limit switch 128 may be an optoelectronic switch, a micro switch or a proximity switch. When assembling, the closing limit switch 128 is triggered by an adjustment screw mounted on the closing main shaft 1232. The jaw is closed to a specified height of 2.5 mm and the length of the adjustment screw is adjusted until the adjustment screw triggers the optoelectronic switch to enter original state. This configuration can ensure accurate closing height, while reducing the requirement on the sizes of parts of the closing main shaft.

The closing limit switch 128 is mounted on the housing 125. When the first linear motion component in the closing mechanism moves to a closing position within a preset range, the closing limit switch 128 may be triggered to transmit a signal to the control unit 114, indicating that the closing stroke comes within a preset range.

When the driving motor 120 is activated, the firing safety switch 126 is at the closing position, and the closing height adjustment shift switch 127 is shifted to a corresponding shift, the program control the closing mechanism operates, the anvil 121 is gradually closed against the cartridge 122. When the closing main shaft 142 comes within a preset position range (often called a green zone), the closing limit switch 128 is triggered, and the motor continues to operate to achieve a corresponding closing height adjustment according to the setting information of the closing height adjustment shift switch 127.

Since tissues squeezed during closing have different thickness, when the closing limit switch 128 is triggered, the control unit 114 receives a closing height preset value chosen by the surgeon through the closing height adjustment shift switch 127 according to the characteristics of the tissue of the patient. Only when the closing height meets the preset standard, the control unit 114 may call a firing program, and transmits an instruction of controlling the driving motor 113 to drive the firing main shaft 1242. In this way, there is no excessive squeezing or inadequate squeezing, to ensure the tissue is squeezed adequately regardless of the thickness, and to ensure stable effect of the staple formation.

A closing switch 1123 and an opening switch 1124 connected to the control unit 114 are arranged outside the handle body 112. The closing switch 1123 is a common switch for closing and firing, so that the closing switch 1123 is required to be triggered no matter a closing action or a firing action is performed.

Only when the control unit 114 detects the closing switch 1123 is triggered, and the firing safety switch 123 is at the first operating position, the control unit 114 transmits an instruction of controlling the driving motor 113 to drive the closing main shaft 1123 to move. Thus when the user operates the electric surgical stapler, the user needs to ensure the firing safety switch 126 is at the first position firstly, and then press the closing switch 1123 to start the closing action When the control unit 114 detects the closing switch 1123 is triggered, and the firing safety switch 126 is at the second operating position, the control unit 114 control the driving motor 113 to drive the firing main shaft 1242 to move.

The closing switch 1123 and the opening switch 1124 can be implemented by Hall switches. If a button with a magnet is arranged outside the handle body 112, the control unit 114 is provided with a Hall switch. The Hall switch may be activated by the magnet. Similarly, the Hall switch may determine whether the switching between the positions of the firing safety switch 126 is detected. The Hall switch may detect the movement of the firing safety switch 126 itself, and may detect the movement of the switching driving lever 1273.

In addition, the control unit 114 can detect whether the closing switch 1123, opening switch 1124 or the firing safety switch 126 is triggered, by the arrangement of an optoelectronic switch, a micro switch or a proximity switch.

The working head 120 also includes a firing limit switch 121A configured to detect the position of the firing main shaft 1242, and transmit information of the position to the control unit 114. When the firing limit switch 121A detects the firing main shaft 1243 comes within the preset position range, the driving motor 113 stops, and the control unit 114 transmits an instruction of prohibiting the driving motor 113 to drive the closing main shaft 1232 to move. That is, when the firing is completed, the control unit 114 may block the closing switch 1123 to disable the closing switch 1123 until a new working head is replaced. The firing switch 121A may be an optoelectronic switch, a micro switch or a proximity switch installed on the housing 125.

The handle 110 is removably connected to the working head 120. When the handle body 112 fits the housing 125, the handle 110 and the working head 120 are assembled together. When the housing 125 is removed from the handle body 112, the handle 110 and the working head 120 are separated from each other. The working head 120 is a circular stapling head. When the handle 110 is assembled with the working head 120, the handle 110 is a straight handle along the longitudinal direction of the working head 120, which conforms with the holding habit, to facilitate, for example, the therapy of gastrointestinal diseases.

The handle body 112 can be connected to or removed from the housing 125 rapidly. If the handle body 112 is provided with an interface part, the housing 125 is provided with a connector accordingly. During assembling, it only needs the housing 125 to be inserted into the handle body 112. The end of the output shaft 1132 is provided with an interface, and the end of the input shaft 1271 is inserted into the output shaft 1132, so the input shaft 1271 and the output shaft 1132 can assembled into a whole, while achieving the connection of the dynamical system.

A data interface 1125 connected to the control unit 114 is arranged inside the handle body 112, configured to connect the closing limit switch 128 and the closing height adjustment shift switch 127. After the assembly of the handle body 112 and the housing 125, the data connector 1252 of the working head 120 is inserted into the data interface 1125.

A release button 1126 is arranged outside the handle body 112. The release button 1126 has a locking position for locking the housing and a release position for unlocking the housing. When the release button 1126 is pressed, the housing 125 is able to be inserted into the handle body 112. When the pressed release button 1126 is loosened, the housing is locked. When it is required to remove the housing 125, the release button 1126 may be pressed firstly to release locking, and then the housing 125 may be pulled out.

It is very convenient for the user to turn the adjustment knob 115 manually in accordance with the specific conditions. The adjustment knob 115 is able to supply a manual mode, to deal with the condition of getting stuck. In addition, when the thickness of the tissue exceeds the maximum closing ability of the device, the manual mode may be activated to make the driving motor 113 get away from the overload endless loop. In the manual mode, the anvil 121 and the cartridge 122 may be opened, or continue to finish the firing.

The electric surgical stapler further includes a replaceable battery pack 117 connected to the handle body 112, and configured to supply power to the driving motor 113. The handle body 112 is provided with an indicator light (not shown) connected to the control unit 114. The indicator light may show the closing state, the firing state or the battery level of the battery pack.

For the electric surgical stapler according to the present disclosure, the control unit 114 can determine whether the closing distance between the anvil 121 and the cartridge 122 is at a preset height based on whether the closing limit switch 128 is triggered. Then the operation of the driving motor 113 is controlled based on the shift where the closing height adjustment shift switch 127 is, so that the closing distance between the anvil and the cartridge is adjusted to be consistent with a closing distance corresponding to the current shift of the closing height adjustment shift switch 127.

Since the device is closed to a maximum height (i.e., a position where the closing optoelectronic switch is triggered) in advance, clearances in the transmission mechanism have been eliminated, and on this basis, the subsequent adjustment of the closing height can be precisely implemented to achieve desired closing height, replacing the old manual adjustment of the closing height. For the case where the height is required to be adjusted, the surgeon only needs to shift the closing height adjustment shift switch to a corresponding shift, to ensure stable effect of the staple formation.

The setting and adjustment of the shift of the closing height adjustment shift switch 127 may be performed before the starting of the whole device, that is, before the distance between the anvil 121 and the cartridge 122 is not closed to the preset closing height. Alternatively, the distance between the anvil 121 and the cartridge 122 is closed to the preset closing height (that is, the closing distance between the anvil 121 and the cartridge 122 is at a preset closing height when the closing limit switch 128 is triggered) firstly, then the shift of the closing height adjustment shift switch 127 is adjusted, and the control unit 114 continues to control the closing mechanism to move according to the closing distance corresponding to the shift where the closing height adjustment shift switch 127 is, so that the closing distance between the anvil 121 and the cartridge 122 is adjusted to be consistent with the closing distance corresponding to the current shift of the closing height adjustment shift switch 127. If the preset closing distance corresponding to the current shift of the closing height adjustment shift switch 127 is consistent with the closing distance between the anvil 121 and the cartridge 122 when the closing limit switch 128 is triggered, the control unit 114 will no longer control the closing mechanism to move, and the subsequent firing procedure will be performed.

In the electric surgical stapler according to the present disclosure, the working head is a disposable component. The handle 110 removeably fit the working head 120. When replacing, only the working head 120 is required to be replaced, while the handle 110 can be used repeatedly after disinfection, to reduce cost. But it is necessary to point out that the above conception of detecting both the closing limit switch 128 and the closing height adjustment shift switch 127 is also applicable for an integrated stapler.

The above working head 120 is a circular stapling head, but can be other types of working heads, for example, a linear stapling head or a straight linear cutter stapling head.

Figure 4:
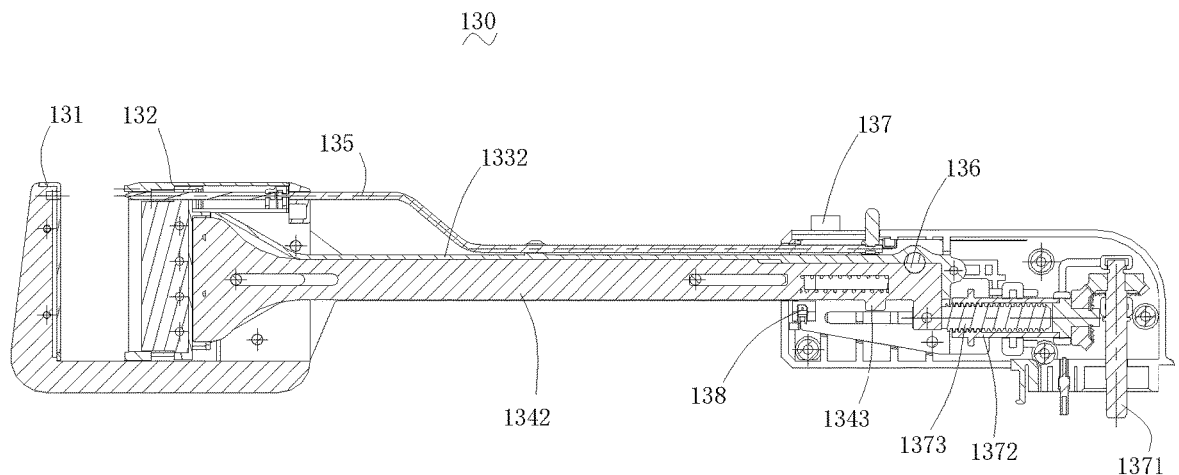
FIG. 4 is a schematic diagram illustrating a cross section of a linear stapling head.

With reference to FIG. 4, a linear working head 130 is provided, with is provided with both a closing limit switch and a closing height adjustment shift switch 133 to detect whether the closing distance meets the requirement. The linear stapler can use a cartridge with a fixed height to match tissues of different thicknesses by adjusting the shift of the closing height adjustment shift switch 133 to set different closing heights for the jaw, without replacing the cartridge.

The circular working head 120 can be replaced by the linear working head 130. The linear working head 130 fits the handle 110, and the mechanical connection form is the same as the above embodiment, with a difference that the device is in a shape of a gun after assembling.

With reference to FIG. 4, the linear working head 130 includes an anvil 131, a cartridge 132, a closing height adjustment shift switch 133, a closing mechanism, a firing mechanism, and a housing 135 housing the closing mechanism and the firing mechanism.

The closing mechanism includes a closing lever 1332. The firing mechanism includes a firing lever 1342. The closing lever 1332 and the firing lever 1342 can move in a straight line together, or move in a straight line relative to one another.

A limit rotation shaft 136 is arranged outside the housing 135. The limit rotation shaft 136 can limit both the closing lever 1332 and the firing lever 1342 in the axial direction, to allow the closing lever 1332 and the firing lever 1342 to move together. When the limit rotation shaft 136 rotates so that the limit rotation shaft 136 is separated from the firing lever 1342 in the axial direction, the firing lever 1342 can move in a straight line relative to the closing lever 1332.

A transmission mechanism is arranged outside the housing 135, including a input shaft 1371, a thread bushing 1372 that is rotatable when driven by tapered teeth, and a screw 1373 in a threaded connection with the thread bushing 1372, and the rotation of the screw 1373 is limited so that the screw 1373 only makes axial movement. A flat fitting portion may be arranged between the screw 1373 and the thread bushing 1372, so that the screw 1373 may only translate in the axial direction. The screw 1373 is connected to the firing lever 1342 to drive the firing lever 1342 to move in a straight line. The limit rotation shaft 136 is equivalent to a firing safety switch which must be operated to switch the closing lever 1332 and the firing lever 1342.

A closing limit switch 138 is arranged inside the housing 135. At closing, the firing lever 1342 may drive the closing lever 1332 to move together, and when firing lever 1342 moves to a specified position, the raised portion 1343 on the firing lever 1342 trigger the closing limit switch 138. At firing, the limit rotation shaft 136 is operated to separate the closing lever 1332 from the firing lever 134, the firing lever 134 does not drive the closing lever 1332 when moving, and the raised portion 1343 moves and triggers the closing limit switch 138 again, to finish the firing of the cartridge.

The closing height adjustment shift switch 133 is arranged on the housing 135 of the linear working head 130. During closing, the surgeon may decide whether the jaw is closed to 2.5 mm or 1.5 mm according to characteristics of the tissue in the surgical site. The closing height adjustment shift switch 133 is initially set to a state for a closing distance of 2.5 mm. When the closing height adjustment shift switch 133 is set to a state for a closing distance of 1.5 mm, the control chip may continue to instruct the motor to make a corresponding number of turns after receiving the signal from the closing limit switch, to adjust the closing height of the jaw. During firing, in addition to the staple ejecting plate, the cartridge 132 is limited in the axial direction, and the firing lever 1342 continues to push the staple ejecting plate, so that the staple ejecting plate moves forward relative to the cartridge 132 to finish the firing.

The linear working head 130 fits the handle 110. Since the device is closed to a maximum height (i.e., a position where the closing optoelectronic switch is triggered) in advance, clearances in the transmission mechanism have been eliminated, and on this basis, the subsequent adjustment of the closing height can be accurately implemented to achieve desired closing height. It can ensure the tissue is squeezed adequately regardless of the thickness, and ensure stable effect of the staple formation, by accurately controlling the closing height.

Figure 5:
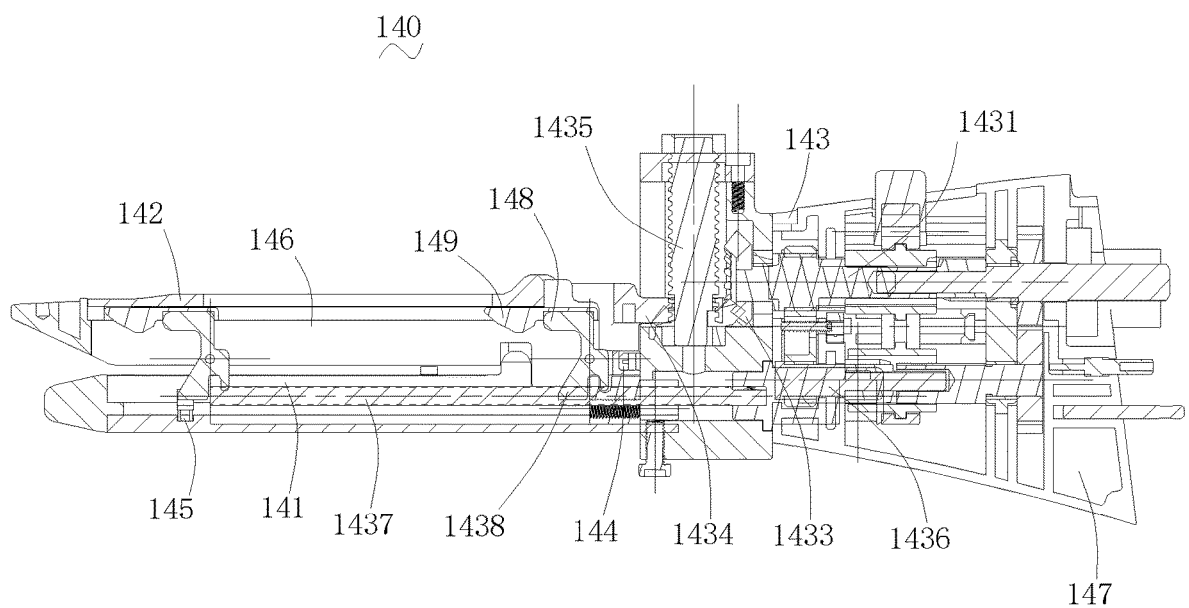
FIG. 5 is a schematic diagram illustrating a cross section of a straight linear cutter stapling head.

With reference to FIG. 5, a straight linear cutter stapling head 140 is provided. The straight linear cutter stapling head 140 can be used with the above handle 110, and the straight linear cutter stapling head 140 is provided with a closing limit switch 144, a firing limit switch 145 and a closing height adjustment shift switch 143. The closing limit switch 144 is configured to detect the closing stroke. The firing limit switch 145 is configured to detect whether the straight linear cutter stapler has completed the firing. The straight linear cutter stapler can use a cartridge with a fixed height to match tissues of different thicknesses by adjusting the shift (2.0 mm, 1.8 mm or 1.5 mm) of the closing height adjustment shift switch 143 to set different closing heights for the jaw, without replacing the cartridge.

The circular working head 120 can be replaced by the straight linear cutter stapling head 140. The straight linear cutter stapling head 140 fits the handle 110, and the mechanical connection form is the same as the above embodiment of the circular working head 120. The switching mechanism between the closing shaft and the firing shaft in this embodiment is identical with the switching mechanism of the circular working head 120.

With reference to FIG. 5, straight linear cutter stapling head 140 includes an anvil 141, a cartridge 142, a closing height adjustment shift switch 143, a closing mechanism, a firing mechanism, and a housing 147 housing the closing mechanism and the firing mechanism.

The closing mechanism of the straight linear cutter stapling head 140 includes a first bevel gear 1433 mounted on the closing main shaft 1431, and a second bevel gear 1434 mounted on the lifting shaft 1435. The rotational motion of the closing main shaft 1431 can be converted into the rotational motion of the lifting shaft 1435 through the first bevel gear 1433 and the second bevel gear 1434. The driving internal thread in the fixed support 146 of the cartridge can engage with the external thread of the lifting shaft 1435 to allow the fixed support 146 to move up and down, thus matching the anvil assembly fastened on the housing 147 to achieve the opening and closing of the jaw of the stapler.

The closing height adjustment shift switch 143 is arranged on the housing 147 of the straight linear cutter stapling head 140. During closing, the surgeon may decide whether the jaw is closed to 2.0 mm, 1.8 mm or 1.5 mm according to characteristics of the tissue in the surgical site. The closing height adjustment shift switch 143 is initially set to a state for a closing distance of 2.0 mm. When the closing height adjustment shift switch 143 is set to a state for a closing distance of 1.8 mm or 1.5 mm, the control chip may continue to instruct the motor to make a corresponding number of turns after receiving the signal from the closing limit switch 144, to adjust the closing height of the jaw.

The firing mechanism of the straight linear cutter stapling head 140 includes a long screw 1437 and a firing sliding block 1438. The rotation of the firing sliding block 1438 is limited by the anvil 141. The rotation of the firing shaft 1436 drives the firing sliding block 1438 to make straight-line movements, the firing sliding block 1438 pushes the staple ejecting sliding block 148 and the cutting blade 149 mounted inside the cartridge to make straight-line movements. The staple ejecting sliding block 148 pushes the staple ejecting plate inside the cartridge to implement the suturing of the tissue. The cutting blade 149 following the staple ejecting sliding block 148 implements the cutting of the tissue. After the staple ejecting sliding block 148 contacts with the firing limit optoelectronic switch mounted inside the anvil 141 and at the distal end of the anvil 141, the program will control the motor to stop forward rotation, and rotate reversely to make the staple ejecting sliding block 148 and the cutting blade 149 return the initial position.

The straight linear cutter stapling head 140 is fit for the handle 110. Since the device is closed to a maximum height (i.e., a position where the closing optoelectronic switch is triggered) in advance, clearances in the transmission mechanism have been eliminated, and on this basis, the subsequent adjustment of the closing height can be accurately implemented to achieve desired closing height. It can ensure the tissue is squeezed adequately regardless of the thickness, and ensure stable effect of the staple formation, by accurately controlling the closing height.

The present invention may be carried out in other specific ways than those herein set forth without departing from the scope and essential characteristics of the invention. The present embodiments are, therefore, to be considered in all respects as illustrative and not restrictive.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

What is claimed is:

1. An electric surgical stapler, comprising:
   a handle, including a handle body, a driving motor and a control unit for controlling the driving motor to operate;
   a working head, including an anvil, a cartridge, a closing mechanism, a firing mechanism, a housing for housing the closing mechanism and the firing mechanism, a closing limit switch configured to transmit information of a closing stroke of the closing mechanism to the control unit, and a closing height adjustment shift switch configured to transmit information of a closing height control shift to the control unit,
   wherein during closing, the control unit is configured to control the closing mechanism to move until the closing limit switch is triggered so that a closing distance between the anvil and the cartridge is at a preset closing height, and the control unit is further configured to control the closing mechanism to move after receiving information transmitted from the closing limit switch, so that the closing distance between the anvil and the cartridge is adjusted to be consistent with a preset closing distance corresponding to a current shift of the closing height adjustment shift switch.

2. The electric surgical stapler of claim 1, wherein the working head further comprises a firing limit switch configured to transmit information of a firing stroke to the control unit, and when the firing limit switch is triggered, the operation of the driving motor is stopped by the control unit.

3. The electric surgical stapler of claim 1, wherein the working head further includes a firing safety switch, the firing safety switch has a first operating position and a second operating position, the firing safety switch allows the driving motor to drive the closing mechanism to operate when the firing safety switch is at the first operating position, and the firing safety switch allows the driving motor to drive the firing mechanism to operate when the firing safety switch is at the second operating position.

4. The electric surgical stapler of claim 1, wherein the closing mechanism includes a first linear motion component configured to drive the anvil to move or drive the cartridge to move, and the firing mechanism includes a second linear motion component configured to push a staple ejecting plate in the cartridge to move.

5. The electric surgical stapler of claim 4, wherein the closing mechanism includes a closing main shaft driven by an output shaft of the driving motor to rotate, the first linear motion component is configured to be driven by the closing main shaft and drive the anvil to move, the firing mechanism includes a firing main shaft driven by the output shaft of the driving motor to rotate, and the second linear motion component is configured to be driven by the firing main shaft and act on the staple ejecting plate in the cartridge.

6. The electric surgical stapler of claim 5, further comprising a firing safety switch having a first operating position and a second operating position, wherein the firing safety switch allows the output shaft to transmit torque to the closing main shaft when the firing safety switch is at the first operating position, and the firing safety switch allows the output shaft to transmit torque to the firing main shaft when the firing safety switch is at the second operating position.

7. The electric surgical stapler of claim 6, wherein a closing switch and an opening switch connected to the control unit are arranged outside the handle body, the control unit is further configured to transmit an instruction of controlling the driving motor to drive the closing main shaft to move when detecting the closing switch is triggered and the firing safety switch is at the first operating position, and the control unit is further configured to transmit an instruction of controlling the driving motor to drive the firing main shaft to move when detecting the closing switch is triggered and the firing safety switch is at the second operating position.

8. The electric surgical stapler of claim 5, further comprising a firing limit switch configured to detect a position of the second linear movement component and transmit position information of the second linear movement component to the control unit, wherein the control unit is further configured to stop the operation of the driving motor when the second linear movement component comes within a preset position range and triggers the firing limit switch.

9. The electric surgical stapler of claim 1, wherein the closing height adjustment shift switch is connected to a different circuit when switching shifts, to transmit different electrical signals to the control unit.

10. The electric surgical stapler of claim 1, wherein the closing height adjustment shift switch is provided with a plurality of shifts, each shift corresponds to a different preset closing distance, each preset closing distance is different from the closing distance between the anvil and the cartridge when the closing limit switch is triggered, or one of the plurality of present closing distances is the same as the closing distance between the anvil and the cartridge when the closing limit switch is triggered.

* * * * *